(12) United States Patent
Addison et al.

(10) Patent No.: US 10,271,779 B2
(45) Date of Patent: Apr. 30, 2019

(54) SYSTEM AND METHOD OF MONITORING AUTOREGULATION

(71) Applicant: COVIDIEN LP, Mansfield, MA (US)

(72) Inventors: Paul S. Addison, Edinburgh (GB); James N. Watson, Dunfermline (GB)

(73) Assignee: Covidien LP, Mansfield, MA (US)

( * ) Notice: Subject to any disclaimer, the term of this patent is extended or adjusted under 35 U.S.C. 154(b) by 324 days.

(21) Appl. No.: 15/194,098

(22) Filed: Jun. 27, 2016

(65) Prior Publication Data
US 2017/0000395 A1   Jan. 5, 2017

Related U.S. Application Data

(60) Provisional application No. 62/186,453, filed on Jun. 30, 2015.

(51) Int. Cl.
| | | |
|---|---|---|
| *A61B 5/00* | (2006.01) | |
| *A61B 5/1455* | (2006.01) | |
| *G16H 50/50* | (2018.01) | |
| *A61B 5/021* | (2006.01) | |
| *G06F 19/00* | (2018.01) | |
| *G16H 50/20* | (2018.01) | |

(52) U.S. Cl.
CPC .......... *A61B 5/14553* (2013.01); *A61B 5/021* (2013.01); *A61B 5/7221* (2013.01); *G06F 19/00* (2013.01); *G16H 50/20* (2018.01); *G16H 50/50* (2018.01); *A61B 5/02108* (2013.01)

(58) Field of Classification Search
CPC ......... A61B 5/02; A61B 5/021; A61B 5/7221; A61B 5/1455; A61B 5/14551; A61B 5/14553; A61B 5/02108; A61B 5/0205; A61B 5/72
See application file for complete search history.

(56) References Cited

U.S. PATENT DOCUMENTS

| | | |
|---|---|---|
| 4,776,339 A | 10/1988 | Schreiber |
| 5,351,685 A | 10/1994 | Potratz |
| 5,482,034 A | 1/1996 | Lewis et al. |
| 5,533,507 A | 7/1996 | Potratz |
| 5,577,500 A | 11/1996 | Potratz |
| 5,584,296 A | 12/1996 | Cui et al. |

(Continued)

FOREIGN PATENT DOCUMENTS

| | | |
|---|---|---|
| EP | 615723 A1 | 9/1994 |
| WO | WO9843071 A1 | 10/1998 |

(Continued)

OTHER PUBLICATIONS

Addison, P. S., et al.; "Low-Oscillation Complex Wavelets," Journal of Sound and Vibration, 2002, vol. 254, Elsevier Science Ltd., pp. 1-30.

(Continued)

*Primary Examiner* — Eric F Winakur
*Assistant Examiner* — Chu Chuan Liu
(74) *Attorney, Agent, or Firm* — Shumaker & Sieffert, P.A.

(57) ABSTRACT

A method for monitoring autoregulation includes using a processor for receiving blood pressure data and oxygen saturation data from a patient, fitting a dynamic model to the blood pressure data and the oxygen saturation data to determine one or more parameters of the dynamic model indicative of autoregulation, and determining the patient's autoregulation status based on the one or more parameters.

19 Claims, 2 Drawing Sheets

(56) References Cited

U.S. PATENT DOCUMENTS

| | | | |
|---|---|---|---|
| 5,626,140 | A | 5/1997 | Feldman et al. |
| 5,803,910 | A | 9/1998 | Potratz |
| 5,934,277 | A | 8/1999 | Mortz |
| 6,385,471 | B1 | 5/2002 | Mortz |
| 6,438,399 | B1 | 8/2002 | Kurth |
| 6,453,183 | B1 | 9/2002 | Walker |
| 6,505,060 | B1 | 1/2003 | Norris |
| 6,510,329 | B2 | 1/2003 | Heckel |
| 6,599,251 | B2 | 7/2003 | Chen et al. |
| 6,668,182 | B2 | 12/2003 | Hubelbank |
| 6,714,803 | B1 | 3/2004 | Mortz |
| 6,754,516 | B2 | 6/2004 | Mannheimer |
| 6,896,661 | B2 | 5/2005 | Dekker |
| 6,987,994 | B1 | 1/2006 | Mortz |
| 7,001,337 | B2 | 2/2006 | Dekker |
| 7,221,969 | B2 | 5/2007 | Stoddart et al. |
| 7,268,873 | B2 | 9/2007 | Sevick-Muraca et al. |
| 7,744,541 | B2 | 6/2010 | Baruch et al. |
| 8,556,811 | B2 | 10/2013 | Brady |
| 2004/0097797 | A1 | 5/2004 | Porges et al. |
| 2005/0004479 | A1 | 1/2005 | Townsend et al. |
| 2005/0033129 | A1 | 2/2005 | Edgar, Jr. et al. |
| 2005/0192488 | A1 | 9/2005 | Bryenton et al. |
| 2005/0192493 | A1 | 9/2005 | Wuori |
| 2007/0004977 | A1 | 1/2007 | Norris |
| 2007/0049812 | A1 | 3/2007 | Aoyagi et al. |
| 2008/0081974 | A1 | 4/2008 | Pav |
| 2008/0146901 | A1 | 6/2008 | Katura et al. |
| 2008/0200785 | A1 | 8/2008 | Fortin |
| 2008/0228053 | A1 | 9/2008 | Wang et al. |
| 2009/0326386 | A1 | 12/2009 | Sethi et al. |
| 2010/0010322 | A1 | 1/2010 | Brady |
| 2010/0030054 | A1 | 2/2010 | Baruch et al. |
| 2010/0049082 | A1 | 2/2010 | Hu et al. |
| 2011/0046459 | A1 | 2/2011 | Zhang et al. |
| 2011/0105912 | A1 | 5/2011 | Widman et al. |
| 2012/0149994 | A1 | 6/2012 | Luczyk et al. |
| 2012/0253211 | A1 | 10/2012 | Brady et al. |
| 2012/0271130 | A1 | 10/2012 | Benni |
| 2013/0190632 | A1 | 7/2013 | Baruch et al. |
| 2014/0073888 | A1 | 3/2014 | Sethi et al. |
| 2014/0275818 | A1 | 9/2014 | Kassem et al. |
| 2014/0278285 | A1 | 9/2014 | Marmarelis et al. |
| 2016/0106372 | A1 | 4/2016 | Addison et al. |
| 2016/0324425 | A1 | 11/2016 | Addison et al. |
| 2016/0345913 | A1 | 12/2016 | Montgomery et al. |
| 2016/0367197 | A1 | 12/2016 | Addison et al. |
| 2017/0000423 | A1 | 1/2017 | Addison et al. |
| 2017/0095161 | A1 | 4/2017 | Addison et al. |
| 2017/0105631 | A1 | 4/2017 | Addison et al. |
| 2017/0105672 | A1 | 4/2017 | Addison et al. |

FOREIGN PATENT DOCUMENTS

| | | |
|---|---|---|
| WO | WO0059374 | 10/2000 |
| WO | WO03000125 A1 | 1/2003 |
| WO | WO03071928 A2 | 9/2003 |
| WO | WO2004075746 A2 | 9/2004 |
| WO | WO2008097411 A1 | 8/2008 |
| WO | WO2016182853 A1 | 11/2016 |

OTHER PUBLICATIONS

Addison, P. S.; "The Illustrated Wavelet Transform Handbook," 2002, IOP Publishing Ltd., Bristol, UK, Ch. 2.

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Barreto, Armando B., et al.; "Adaptive LMS Delay Measurement in dual Blood Volume Pulse Signals for Non-Invasive Monitoring," *IEEE*, pp. 117-120 (1997).

Bassan, Haim, et al.; "Identification of pressure passive cerebral perfusion and its mediators after infant cardiac surgery," Pediatric Research Foundation, vol. 57, No. 1, 2005; pp. 35-41.

Belal, Suliman Yousef, et al.; "A fuzzy system for detecting distorted plethysmogram pulses in neonates and paediatric patients," *Physiol. Meas.*, vol. 22, pp. 397-412 (2001).

Brady, Ken M., et al.; "Continuous Measurement of Autoregulation by Spontaneous Fluctuations in Cerebral Perfusion Pressure Comparison of 3 Methods," NIH Public Access Author Manuscript, Stroke, 2008, 39(9), pp. 1-13.

Brady, Ken M., et al.; "Continuous time-domain analysis of cerebrovascular autoregulation using near-infrared spectroscopy," American Stroke Association, DOI:10.1161/strokeaha.107.485706, Aug. 2007, pp. 2818-2825.

Brady, Ken M., et al.; "Monitoring cerebral blood flow pressure autoregulation in pediatric patients during cardiac surgery," Stroke 2010;41:1957-1962 (http://stroke.ahajournals.org/content/41/9/1957.full).

Brady, Ken M., et al.; "Noninvasive Autoregulation Monitoring with and without Intracranial Pressure in a Näive Piglet Brain," Neuroscience in Anesthesiology and Perioperative Medicine, 2010, vol. 111, No. 1, International Anesthesia Research Society, pp. 191-195.

Brady, Kenneth, et al.; "Real-Time Continuous Monitoring of Cerebral Blood Flow Autoregulation Using Near-Infrared Spectroscopy in Patients Undergoing Cardiopulmonary Bypass," Stroke, 2010, 41, American Heart Association, Inc., pp. 1951-1956.

Caicedo, Alexander, et al.; "Cerebral Tissue Oxygenation and Regional Oxygen Saturation Can be Used to study Cerebral Autoregulation in Prematurely Born Infants," Pediatric Research, vol. 69, No. 6, Jun. 1, 2011, pp. 548-553.

Caicedo, Alexander, et al.; "Detection of cerebral autoregulation by near-infrared spectroscopy in neonates: performance analysis of measurement methods," Journal of Biomedical Optics 17 (11) pp. 117003-1-117003-9 (Nov. 2012).

Chan, K.W., et al.; "17.3: Adaptive Reduction of Motion Artifact from Photoplethysmographic Recordings using a Variable Step-Size LMS Filter," IEEE, pp. 1343-1346 (2002)+A10.

Chen, Li, et al.; "The role of pulse oximetry plethysmographic waveform monitoring as a marker of restoration of spontaneous circulation: a pilot study," Chin Crit Care Med, 2015, vol. 27, No. 3, pp. 203-208.

Chen, Liangyou, et al.; "IS respiration-induced variation in the photoplethysmogram associated with major hypovolemia in patients with actue tramatic injuries," SHOCK, vol. 34, No. 5, pp. 455-460 (2010).

Cheng, Ran, et al.; "Noninvasive optical evaluation of spontaneous low frequency oscillations in cerebral hemodynamics", Neuroimage, Academic Press, vol. 62, No. 3, May 24, 2012, pp. 1445-1454.

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Cysewska-Sobusaik, Anna; "Metrological Problems With noninvasive Transillumination of Living Tissues," *Proceedings of SPIE*, vol. 4515, pp. 15-24 (2001).

Czosnyka, Marek, et al.; "Monitoring of cerebrovascular autoregulation: Facts, Myths, and Missing Links," Neurocrit Care (2009) 10:373-386.

Daubechies, Ingrid, et al.; "A Nonlinear Squeezing of the Continuous Wavelet Transform Based on Auditory Nerve Models," Princeton University, 1996, Acoustic Processing Department, NY, pp. iii, 1-17.

Daubechies, Ingrid, et al.; "Synchrosqueezed Wavelet Transforms: an Empirical Mode Decomposition-like Tool," Princeton University, 2010, Applied and Computational Harmonic Analysis, pp. 1-32.

Dias, Celeste, et al.; "Optimal Cerebral Perfusion Pressure Management at Bedside: A Single-Center Pilot Study," Neurocritical care, vol. 23, No. 1, Jan. 8, 2015; pp. 92-102; ISSN: 1541-6933.

(56) References Cited

OTHER PUBLICATIONS

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?13 An In-Vitro Investigation," *Proceedings of the 20th Annual International conference of the IEEE Engie in Medicine and Biology Society*, vol. 20, No. 6, p. 3072-3075, 1998.

Eichhorn, Lars, et al.; "Evaluation of newar-infrared spectroscopy under apnea-dependent hypoxia in humans," Journal of Clinical Monitoring and Computing, vol. 29, No. 6, Feb. 4, 2015, pp. 749-757.

Gao, Yuanjuin, et al.; "Response of cerebral tissue oxygenation and arterial blood pressure to postural change assessed by wavelet phase coherence analysis", 2014 7th International conference on Biomedical Engineering and Informatics, IEEE, Oct. 14, 2014, pp. 373-377.

Ge, Z.; "Significance tests for the wavelet cross spectrum and wavelet linear coherence," Annales Geophysicae, 2008, 26, Copernicus Publications on behalf of European Geosciences Union, pp. 3819-3829.

Gesquiere, Michael J., et al., "Impact of withdrawal of 450 ML of blook on respiration-induced oscillations of the ear plethysmographic waveform," Journal of Clinical Monitoring and Computing (2007) 21:277-282.

Goldman, Julian M.; "Masimo Signal Extraction Pulse Oximetry," *Journal of Clinical Monitoring and Computing*, vol. 16, pp. 475-483 (2000).

Gommer, Erik D., et al.; "Dynamic cerebral autoregulation: different signal processing methods without influence on results and reproducibility"; Medical & Biological Engineering & Computer; vol. 48, No. 12, Nov. 4, 2010; pp. 1243-1250.

Hamilton, Patrick S., et al.; "Effect of Adaptive Motion-Artifact Reduction on QRS Detection," *Biomedical Instrumentation & Technology*, pp. 197-202 (May-Jun. 2000).

Huang, J., et al.; "Low Power Motion Tolerant Pulse Oximetry," Anesthesia & Analgesia 2002 94: S103.

Johansson, A.; "Neural network for photoplethysmographic respiratory rate monitoring," *Medical & Biological Engineering & Computing*, vol. 41, pp. 242-248 (2003).

Kaestle, S.; "Determining Artefact Sensitivity of New Pulse Oximeters in Laboratory Using Signals Obtained from Patient," *Biomedizinische Technik*, vol. 45 (2000).

Kim, J.M., et al.; "Signal Processing Using Fourier & Wavelet Transform for pulse oximetry," pp. II-310-II-311 (2001).

Kirkham, S.K., et al.; "A new mathematical model of dynamic cerebral autoregulation based on a flow dependent feedback mechanism; Dynamic cerebral autoregulation modelling," Physiological Measurement, Institute of Physics Publishing, vol. 22, No. 3, Aug. 1, 2001; (13 pgs.).

Leahy, Martin J., et al.; "Sensor Validation in Biomedical Applications," *IFAC Modelling and Control in Biomedical Systems*, Warwick, UK; pp. 221-226 (1997).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Lee, Jennifer K., et al.; A pilot study of cerebrovascular reactivity autoregulation after pediatric cardiac arrest, Resuscitation 85, 2014, Elsevier Ireland Ltd., pp. 1387-1393.

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Massart, Desire L., et al.; "Least Median of Squares: a Robust Method for Outlier and Model Error Detection in Regression and Calibration," Analytica Chimica Acta, 1986, Elsevier Science Publishers B.V., The Netherlands, pp. 171-179.

McGrath, S.P., et al.; "Pulse oximeter plethysmographic waveform changes in awake, spontaneously breathing, hypovolemic volunteers," Anesth. Analg. vol. 112 No. 2, pp. 368-374 (2010).

Montgomery, Dean, et al.; "Data cluestering methods for the determination of cerebral autoregulation functionality," Journal of Clinical Monitoring and Computing, vol. 30, No. 5, Sep. 16, 2015, pp. 661-668.

Morren, G., et al.; "Detection of autoregulation in the brain of premature infants using a novel subspace-based technique," 23rd Annual International Conference of IEEE Engineering in Medicine and Biology Society, Oct. 2001; pp. 1-4.

Morren, Geert, et al.; "Quantitation of the concordance between cerebral intravascular oxygenation and mean arterial blood pressure for the detection of impaired autoregulation," 29th Annual Meeting of the International Society on Oxygen Transport to Tissue, UofP, Aug. 2001; pp. 1-5.

Neumann, R., et al.; "Fourier Artifact suppression Technology Provides Reliable $SpO_2$," Anesthesia & Analgesia 2002, 94: S105.

Obrig, Hellmuth, et al.; "Spontaneous low frequency oscillations of cerebral heodynamics and metabolism in human adults," NeuroImage 12, 623-639 (2000).

Odagiri, Y.; "Pulse Wave Measuring Device," *Micromechatronics*, vol. 42, No. 3, pp. 6-11 (published Sep. 1998) (Article in Japanese—contains English summary of article).

Ono, Masahiro, et al.; "Validation of a stand-alone near-infrared spectroscopy system for monitoring cerebral autoregulaiton during cardiac surgery," International Anethesia Research Society, Jan. 2013, vol. 116, No. 1, pp. 198-204.

Panerai, B.; "Cerebral Autoregulation: from models to clinical Applications," Cardiovascular Engineering: an International Journal, vol. 8, No. 1, Nov. 28, 2007, (28 pgs.).

Payne, Stephen J., et al.; "Tissue Oxygenation Index as a Measure of Cerebral Autoregulation," Biomedial Engineering, Feb. 2004, Innsbruck, Austria, pp. 546-550.

Reinhard, Matthias, et al.; "Spatial mapping of dynamic cerebral autoregulation by multichannel near-infrared spectrosccopy in high-grade carotid artery disease", International Society for optical Engineering, SPIE, vol. 19, No. 9, Sep. 1, 2014, p. 97005.

Reinhard, Matthias, et al.; "Oscillatory cerebral hemodynamics—the macro- vs. microvascular level," Journal of the Neurological Sciences 250 (2006) 103-109.

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Rowley, A.B., et al.; "Synchronization between arterial blood pressure and cerebral oxyhaemoglobin concentration investigated by wavelet cross-correlation," Physiol. Meas., vol. 28, No. 2, Feb. 2007, pp. 161-173.

Shamir, M., et al.; "Pulse oximetry plethysmographic waveform during changes in blood volume," British Journal of Anaesthesia 82(2): 178-81 (1999).

Sorensen, Henrik, et al.; "A note on arterial to venous oxygen saturation as reference for NIRS-determined frontal lobe oxygen saturation in healthy humans," Frontiers in Physiology, vol. 4, Art. 403, Jan. 2014, pp. 1-3.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Tsuji, Miles, et al.; "Cerebral intravascular oxygenation correlates with mean arterial pressure in critically ill premature infants," American Academy of Pediatrics, 2000; 106; pp. 625-632.

Wagner, Bendicht P., et al.; "Dynamic cerebral autoregulatory response to blood pressure rise measured by near-infrared spectroscopy and intracranial pressure," Critical Care Medicine 2002, vol. 30, No. 9, pp. 2014-2021.

(56) References Cited

OTHER PUBLICATIONS

Whitaker, E., et al.; "Cerebrovascular Autoregulation After Pediatric Cardiac Arrest," NEURO-85, 2012, 2 pgs.

Williams, Monica, et al.; "Intraoperative blood pressure and Cerebral perfusion: strategies to clarify hemodynamic goals," Paediatric Anaesthesia, vol. 24, No. 7, Jul. 12, 2014; pp. 657-667; XP055331904.

Wong, Flora Y., et al.; "Impaired Autoregulation in preterm infants identified by using spatially resolved spectroscopy," American Academy of Pediatrics DOI:10.1542 (2008) e604-611.

Wu Dongmei, et al.; "Na*/H* Exchange inhibition delays the onset of hypovolemic circulatory shock in pigs," SHOCK, vol. 29, No. 4, pp. 519-525 (2008).

Wu, et al.; "Using synchrosqueezing transform to discover breathing dynamics from ECG signals," arXiv:1105.1571, vol. 2, Dec. 2013, pp. 1-9.

Wu, Hau-tieng, et al.; "Evaluating physiological dynamics via Synchrosqueezing: Prediction of Ventilator Weaning," Journal of Latex Class Files, vol. 11, No. 4, Dec. 2012, pp. 1-9.

Zhang, Rong, et al.; "Transfer function analysis of dynamic cerebral autoregulation in humans," 1998 the American Physiological Society; pp. H233-241.

Zweifel, Christian, et al.; "Continuous time-domain monitoring of cerebral autoregulation in neurocritical care," Medical Engineering & Physics, Elsevier Ltd., vol. 36, No. 5, 2014, pp. 638-645.

U.S. Appl. No. 15/648,665, filed Jul. 13, 2017, Dean Montgomery.

International Search Report and Written Opinion from International Application No. PCT/US2016/039865, dated Sep. 16, 2016, 9 pp.

U.S. Appl. No. 15/666,167, filed Aug. 1, 2017, naming inventors Addison et al.

International Preliminary Report on Patentability from International Application No. PCT/US2016/039865, dated Jan. 11, 2018, 7 pp.

S.K. Kirkham et al.; "A new mathematical model of dynamic cerebral autoregulation based on a flow dependent feedback mechanism; Dynamic cerebral autoregulation modelling," Physiological Measurement, Institute of Physics Publishing, vol. 22, No. 3, Aug. 1, 2001; (13 pgs.).

Panerai, "Cerebral Autoregulation: from models to clinical Applications," Cardiovascular Engineering: an International Journal, vol. 8, No. 1, Nov. 28, 2007, (28 pgs.).

International Search Report & Written Opinion for PCT Application No. PCT/US2016/039865 dated Sep. 16, 2016; 12 pgs.

Chuan et al., "Is cerebrovascular autoregulation associated with outcomes after major noncardiac surgery? A prospective observational pilot study," Acta Anaesthesiol Scand., Aug. 5, 2018, 10 pages.

Examination Report from counterpart European Application No. 16744965.1, dated Jan. 11, 2019, 4 pp.

SYSTEM AND METHOD OF MONITORING AUTOREGULATION

CROSS-REFERENCE TO RELATED APPLICATION

This application claims priority to and the benefit of Provisional Application No. 62/186,453, entitled "SYSTEM AND METHOD OF MONITORING AUTOREGULATION," filed Jun. 30, 2015, which is herein incorporated by reference in its entirety for all purposes.

BACKGROUND

The present disclosure relates generally to medical devices and, more particularly, to systems and methods of monitoring autoregulation.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, medical professionals often desire to monitor certain physiological parameters of their patients. In some cases, clinicians may wish to monitor a patient's autoregulation. Autoregulation is a physiological process that attempts to maintain an optimal cerebral blood flow to supply appropriate levels of oxygen and nutrients to the brain. During autoregulation, cerebral arterioles dilate or constrict to maintain optimal blood flow. For example, as cerebral pressure decreases, cerebral arterioles dilate in an attempt to maintain blood flow. As cerebral pressure increases, cerebral arterioles constrict to reduce the blood flow that could cause injury to the brain. If the patient's autoregulation process is not functioning properly, the patient may experience inappropriate cerebral blood flow, which may have negative effects on the patient's health. In particular, a drop in cerebral blood flow may cause ischemia, which may result in tissue damage or death of brain cells. An increase in cerebral blood flow may cause hyperemia, which may result in swelling of the brain or edema.

Some existing systems for monitoring autoregulation may determine a patient's autoregulation status based on various physiological signals. However, existing systems for monitoring autoregulation may not adequately consider or analyze dynamic relationships between the physiological signals used to determine the patient's autoregulation status. Accordingly, the autoregulation status determined by such existing systems may be inaccurate or imprecise.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A physician may monitor a patient's autoregulation through the use of various monitoring devices and systems. In accordance with the present disclosure, a patient's autoregulation may be monitored by analyzing a dynamic relationship between the patient's blood pressure (e.g., arterial blood pressure) and the patient's oxygen saturation (e.g., regional oxygen saturation). For example, it is expected that the patient's oxygen saturation will initially follow (e.g., track or trend with) a change in the patient's blood pressure. Thereafter, an intact autoregulation system will respond by adjusting cerebral blood flow, thereby causing the oxygen saturation to return approximately to its previous (e.g., baseline) value. However, an impaired autoregulation system may not adequately adjust cerebral blood flow, and thus, the oxygen saturation may fluctuate with the blood pressure or fail to return to its previous value within a certain amount of time.

In the present embodiments, a model (e.g., dynamic model) of a response of oxygen saturation to a change in blood pressure may be constructed. The dynamic model may be used to parameterize a patient's autoregulation function. For example, during patient monitoring, the dynamic model may be fitted to patient data (e.g., blood pressure data and oxygen saturation data), and the parameters of the dynamic model may be identified (e.g., via a parametric search). The parameters may be indicative of the oxygen saturation response to changes in blood pressure and of the patient's autoregulation status. In particular, the parameters may enable a determination of whether the patient's autoregulation system is intact or impaired. In some embodiments, the parameters may enable a determination of a degree of impairment of the patient's autoregulation system. Furthermore, in some embodiments, the systems and methods may be configured to provide information indicative of the patient's autoregulation status to the medical professional, as discussed in more detail below.

Figure 1:
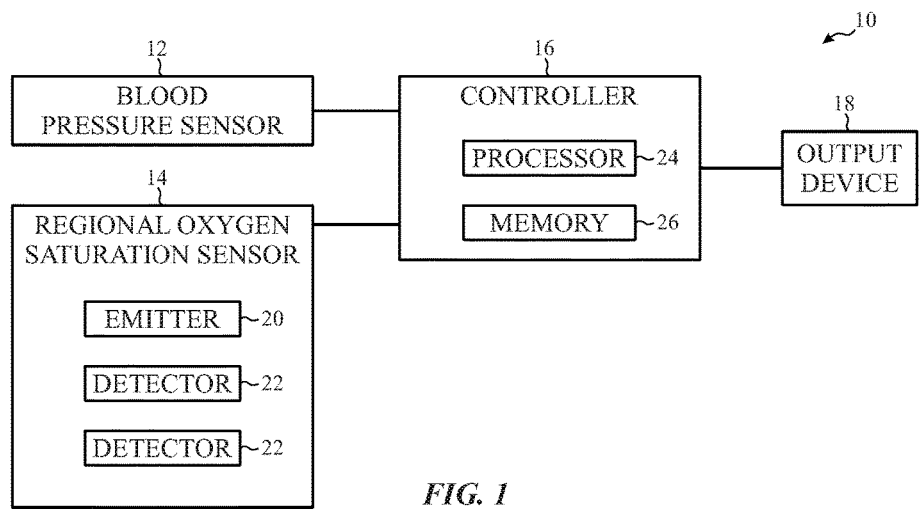
FIG. 1 is a block diagram of an embodiment of a system for monitoring a patient's autoregulation.

FIG. 1 illustrates an embodiment of a system 10 for monitoring autoregulation, in accordance with the present disclosure. As shown, the system 10 includes a blood pressure sensor 12, an oxygen saturation sensor 14 (e.g., a regional oxygen saturation sensor), a controller 16, and an output device 18. The blood pressure sensor 12 may be any sensor or device configured to obtain the patient's blood pressure (e.g., arterial blood pressure). For example, the blood pressure sensor 12 may include a blood pressure cuff for non-invasively monitoring blood pressure or an arterial line for invasively monitoring blood pressure. In certain embodiments, the blood pressure sensor 12 may include one or more pulse oximetry sensors. In some such cases, the patient's blood pressure may be derived by processing time delays between two or more characteristic points within a single plethysmography (PPG) signal obtained from a single pulse oximetry sensor. Various techniques for deriving blood pressure based on a comparison of time delays between certain components of a single PPG signal obtained from a single pulse oximetry sensor are described in U.S. Publication No. 2009/0326386, entitled "Systems and Methods for Non-Invasive Blood Pressure Monitoring," the entirety of which is incorporated herein by reference. In other cases, the patient's blood pressure may be continuously, non-invasively monitored via multiple pulse oximetry sensors placed at multiple locations on the patient's body. As described in U.S. Pat. No. 6,599,251, entitled "Continuous Non-invasive Blood Pressure Monitoring Method and Apparatus," the entirety of which is incorporated herein by reference, multiple PPG signals may be obtained from the multiple pulse oximetry sensors, and the PPG signals may be compared against one another to estimate the patient's blood pressure. Regardless of its form, the blood pressure sensor 12 may be configured to generate a blood pressure signal indicative of the patient's blood pressure (e.g., arterial blood pressure) over time. As discussed in more detail below, the blood pressure sensor 12 may provide the blood pressure signal to the controller 16 or to any other suitable processing device to enable evaluation of the patient's autoregulation status.

As shown, the oxygen saturation sensor 14 may be a regional oxygen saturation sensor configured to generate an oxygen saturation signal indicative of blood oxygen saturation within the venous, arterial, and capillary systems within a region of the patient. For example, the oxygen saturation sensor 14 may be configured to be placed on the patient's forehead and may be used to calculate the oxygen saturation of the patient's blood within the venous, arterial, and capillary systems of a region underlying the patient's forehead (e.g., in the cerebral cortex).

In such cases, the oxygen saturation sensor 14 may include an emitter 20 and multiple detectors 22. The emitter 20 may include at least two light emitting diodes (LEDs), each configured to emit at different wavelengths of light, e.g., red or near infrared light. In one embodiment, the LEDs of the emitter 20 emit light in the range of about 600 nm to about 1000 nm. In a particular embodiment, one LED of the emitter 20 is configured to emit light at about 730 nm and the other LED of the emitter 20 is configured to emit light at about 810 nm. One of the detectors 22 is positioned relatively "close" (e.g., proximal) to the emitter 20 and one of the detectors 22 is positioned relatively "far" (e.g., distal) from the emitter 22. Light intensity of multiple wavelengths may be received at both the "close" and the "far" detectors 22. For example, if two wavelengths are used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation ($rSO_2$) signal for the target tissues over time. As discussed in more detail below, the oxygen saturation sensor 14 may provide the regional oxygen saturation signal to the controller 16 or to any other suitable processing device to enable evaluation of the patient's autoregulation status.

In operation, the blood pressure sensor 12 and the oxygen saturation sensor 14 may each be placed on the same or different parts of the patient's body. Indeed, the blood pressure sensor 12 and the oxygen saturation sensor 14 may in some cases be part of the same sensor or supported by a single sensor housing. For example, the blood pressure sensor 12 and the oxygen saturation sensor 14 may be part of an integrated oximetry system configured to non-invasively measure blood pressure (e.g., based on time delays in a PPG signal) and regional oxygen saturation. One or both of the blood pressure sensor 12 or the oxygen saturation sensor 14 may be further configured to measure other parameters, such as hemoglobin, respiratory rate, respiratory effort, heart rate, saturation pattern detection, Bispectral™ index (BIS) or electromyography (EMG) response to electrical stimulus, or the like. While an exemplary system 10 is shown, the exemplary components illustrated in FIG. 1 are not intended to be limiting. Indeed, additional or alternative components and/or implementations may be used.

As noted above, the blood pressure sensor 12 may be configured to provide the blood pressure signal to the controller 16, and the oxygen saturation sensor 14 may be configured to provide the oxygen saturation signal to the controller 16. In certain embodiments, the controller 16 is an electronic controller having electrical circuitry configured to process the various received signals. In particular, the controller 16 may be configured to process the blood pressure signal and the oxygen saturation signal to evaluate the patient's cerebral autoregulation status. Although the blood pressure sensor 12 and the oxygen saturation sensor 14 may be configured to provide their respective signals or data directly to the controller 16, in certain embodiments, the signals or data obtained by the blood pressure sensor 12 and/or the oxygen saturation sensor 14 may be provided to one or more intermediate processing devices (e.g., specialized monitor, such as a blood pressure monitor or an oxygen saturation monitor, or the like), which may in turn provide processed signals or data to the controller 16.

Figure 2A:
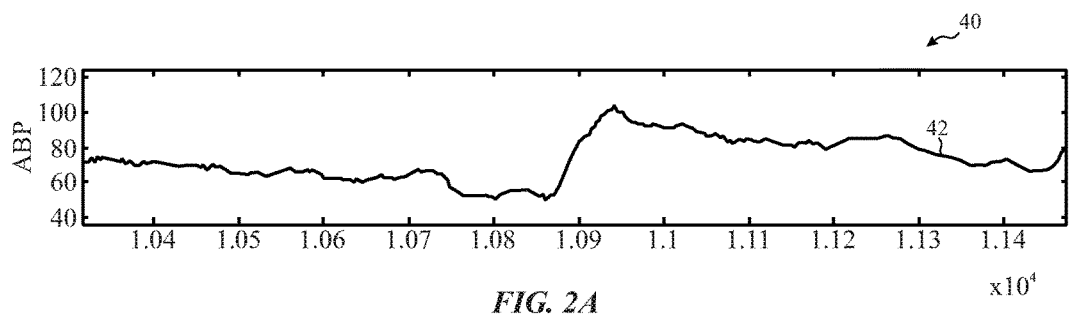
FIGS. 2A and 2B are an example of graphs illustrating oxygen saturation and blood pressure over time.
Figure 2B:
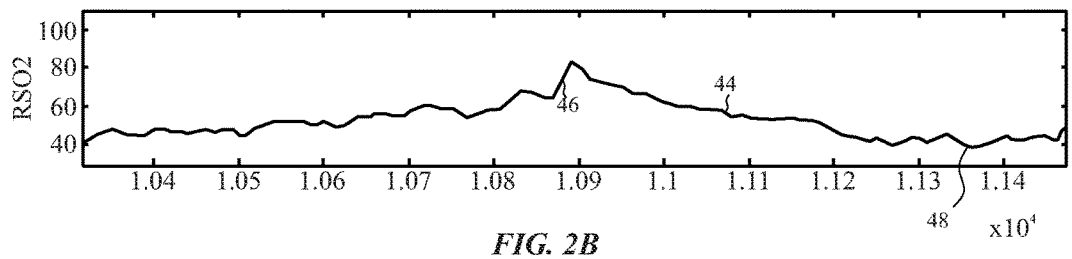

With the foregoing in mind, FIGS. 2A and 2B are examples of graphs 40 illustrating a blood pressure signal 42 and an oxygen saturation signal 44 of a patient, respectively. As shown at region 46, the oxygen saturation signal 44 may initially follow (e.g., track or trend with) a change in the patient's blood pressure signal 42. An intact autoregulation system will respond by adjusting cerebral blood flow, thereby causing the oxygen saturation to return approximately to its previous (e.g., baseline) value, as shown at region 48. However, an impaired autoregulation system may not adequately adjust cerebral blood flow, and thus, the oxygen saturation may fluctuate with the blood pressure or fail to return to its previous value within a certain amount of time.

Returning to FIG. 1, in the illustrated embodiment, the controller 16 includes a processor 24 and a memory device 26. The controller 16 may also include one or more storage devices. The controller 16, or other suitable processing device, may be configured to construct a model of a relationship between blood pressure (e.g., arterial blood pressure) and oxygen saturation (e.g., regional oxygen saturation). In particular, the controller 16 may be configured to construct a dynamic model (e.g., to account for time-dependent changes in the state of the system) of a response of oxygen saturation to a change in blood pressure (e.g., based on empirical data). The dynamic model may be constructed via any suitable technique. For example, blood pressure data and oxygen saturation data from a population of patients or from the monitored patient may be recorded and subjected to data analysis to generate the dynamic model.

In some embodiments, one or more dynamic models related to autoregulation may be constructed and/or stored in the memory device 26 of the controller 16, or other suitable storage device accessible by the controller 16. The controller 16 may be configured to access (e.g., from the memory device 26) the dynamic model and/or to use the dynamic model to determine the patient's autoregulation status. In some embodiments, the controller 16 may construct, access, and/or select an appropriate dynamic model from the memory device 26. For example, the controller 16 may select a dynamic model constructed for the particular patient (e.g., based on data previously obtained from the patient and/or based on characteristics (e.g., age, gender, physiological condition, or the like) of the monitored patient as input by a user and/or a sensor and/or based on operator preferences.

During patient monitoring, the controller 16 may be configured to fit the dynamic model to patient data (e.g., blood pressure data obtained by the blood pressure sensor 12 and oxygen saturation data obtained by the oxygen saturation sensor 14), and to determine (e.g., estimate and/or optimize) parameters of the dynamic model (e.g., via a parametric search). The parameters may be indicative of the oxygen saturation response to changes in blood pressure and may be indicative of the patient's autoregulation status. The controller 16 may be configured to determine whether the patient's autoregulation system is intact or impaired, and/or may be configured to determine a degree of impairment of the patient's autoregulation system, based on the parameters.

With reference to FIG. 1, the processor 24 of the controller 16 may be used to execute software, such as software for carrying out any of the techniques disclosed herein, such as processing the blood pressure signals and/or oxygen saturation signals, constructing the dynamic model, fitting the dynamic model to patient data, estimating parameters, analyzing parameters indicative of the oxygen saturation response and/or autoregulation, determining the patient's autoregulation status based on the parameters, providing information indicative of the patient's autoregulation status on a display, and so forth. Moreover, the processor 24 may include multiple microprocessors, one or more "general-purpose" microprocessors, one or more special-purpose microprocessors, and/or one or more application specific integrated circuits (ASICS), or some combination thereof. For example, the processor 24 may include one or more reduced instruction set (RISC) processors.

Furthermore, the memory device 26 may include a volatile memory, such as random access memory (RAM), and/or a nonvolatile memory, such as ROM. The memory device 26 may include one or more tangible, non-transitory, machine-readable media collectively storing instructions executable by the processor 24 to perform the methods and control actions described herein. Such machine-readable media can be any available media that can be accessed by the processor 24 or by any general purpose or special purpose computer or other machine with a processor. The memory device 26 may store a variety of information and may be used for various purposes. For example, the memory device 26 may store processor-executable instructions (e.g., firmware or software) for the processor 24 to execute, such as instructions for carrying out any of the techniques discloses herein, such as processing the blood pressure signal and/or the oxygen saturation signal, constructing a dynamic model, fitting a dynamic model to patient data, estimating parameters, analyzing parameters indicative of oxygen saturation response and/or autoregulation, determining the patient's autoregulation status based on the parameters, providing information indicative of the patient's autoregulation status on a display, or the like. The storage device(s) (e.g., nonvolatile storage) may include read-only memory (ROM), flash memory, a hard drive, or any other suitable optical, magnetic, or solid-state storage medium, or a combination thereof. The storage device(s) may store data (e.g., the blood pressure signal, the oxygen saturation signal, the dynamic model(s), parameters, etc.), instructions (e.g., software or firmware for processing the blood pressure signal and/or the oxygen saturation signal, constructing the dynamic model, fitting the dynamic model to patient data, estimating parameters, analyzing parameters indicative of the oxygen saturation response and/or autoregulation, determining the patient's autoregulation status based on the parameters, providing information indicative of the patient's autoregulation status on a display, or the like), predetermined values, ranges, and/or thresholds, and any other suitable information.

As shown, the system 10 includes the output device 18. In some embodiments, the controller 16 may be configured to provide signals indicative of the patient's autoregulation status to the output device 18. As discussed in more detail below, the controller 16 may be configured to generate an alarm signal indicative of the patient's autoregulation status and to provide the alarm signal to the output device 18. The output device 18 may include any device configured to receive signals (e.g., the signal indicative of the patient's autoregulation status, the alarm signal, or the like) from the controller 16 and visually and/or audibly output information indicative of the patient's autoregulation status (e.g., the estimated parameters, a graph, a numerical indicator, a text message, or the like). For instance, the output device 18 may include a display configured to provide a visual representation of the patient's autoregulation status as determined by the controller 16. Additionally or alternatively, the output device 18 may include an audio device configured to provide sounds in accordance with the patient's autoregulation status. The output device 18 may be any suitable device for conveying such information, including a computer workstation, a server, a desktop, a notebook, a laptop, a handheld computer, a mobile device, or the like. In some embodiments, the controller 16 and the output device 18 may be part of the same device or supported within one housing (e.g., a computer or monitor).

Figure 3A:
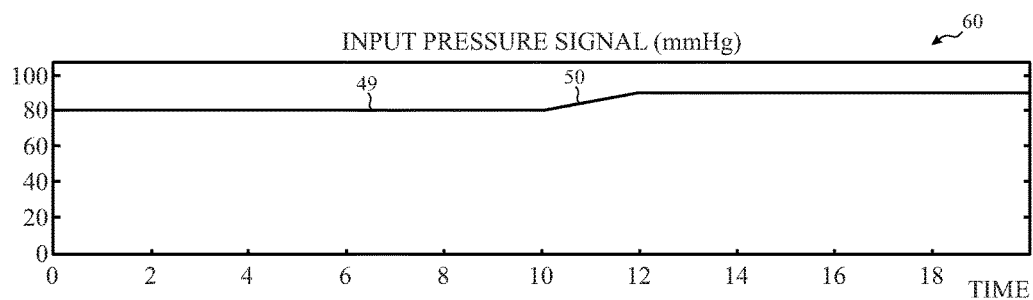
FIGS. 3A and 3B are an example of a model of a response of oxygen saturation to a change in blood pressure.
Figure 3B:
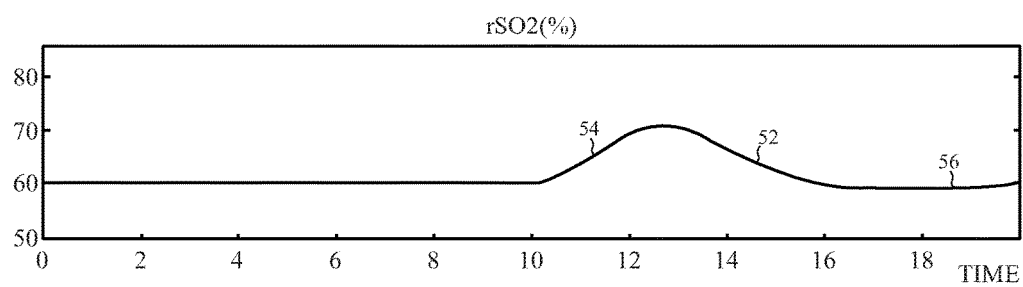

As noted above, a model (e.g., a dynamic model) defining a response of oxygen saturation to changes in blood pressure may be constructed. The dynamic model may be constructed via any suitable technique. In some embodiments, blood pressure data and oxygen saturation data from a population of patients or from a particular patient may be recorded, observed, and/or subjected to data analysis to generate the dynamic model. In certain embodiments, the dynamic model may be based on a simplified idealization of the expected cerebral response to changes in blood pressure. For example, the cerebral response may be modeled as a damped dynamic oscillator driven by blood pressure. An example of such a model may have the following form:

$$A\ddot{x}^a + B\dot{x}^b + Cx^c + D = P^* \qquad (1)$$

where x is an oxygen saturation value, $\dot{x}$ is the first derivative of x, $\ddot{x}$ is the second derivative of x, $P^*$ is a pressure forcing function (e.g., a change in pressure over time), and D is a constant. The parameters (e.g., A, a, B, b, C, and c) define the dynamic model behavior in response to the forcing function P* FIGS. 3A and 3B show an example of a model 60 of an oxygen saturation response based on equation (1), solved with a fourth order Runge-Kutta solver. As shown, when a blood pressure signal input 49 increases at region 50 as shown in FIG. 3A, an oxygen saturation response signal 52 increases at region 54 and subsequently returns to its previous (e.g., baseline) value at region 56 over time, as shown in FIG. 3B.

As discussed above, once the dynamic model is constructed, the model may be used by the controller 16 to monitor a patient's autoregulation status. In particular, the dynamic model may be used to parameterize the patient's autoregulation function. For example, during patient monitoring, the controller 16 may fit the dynamic model to patient data (e.g., blood pressure data obtained by the blood pressure sensor 12 and oxygen saturation data obtained by the oxygen saturation sensor 14). The controller 16 may determine (e.g., estimate and/or optimize) parameters (e.g., parameters A, a, B, b, C, and c of Equation (1)) via a parametric search, or other suitable technique. In some embodiments, the controller 16 may be configured to compare the determined parameters to a database of parameters (e.g., values, ranges, and/or thresholds related to the respective parameters) stored in the memory device 26 or other suitable storage device to facilitate determination of the patient's autoregulation status.

As noted above, the parameters may be indicative of the oxygen saturation response to changes in blood pressure and may be indicative of the patient's autoregulation status. Thus, determination of the parameters, analysis of the parameters, and/or comparison of the parameters to the values and/or thresholds (e.g., stored in the memory device 26) may enable the controller 16 to determine whether the patient's autoregulation system is intact or impaired. Certain parameter values or combinations of parameter values may indicate intact autoregulation, while some values may indicate moderately impaired autoregulation, and other values may indicate severely impaired autoregulation. Such parameterization may enable determination of a degree of impairment of the patient's autoregulation system. In some embodiments, the controller 16 may be configured to provide signals indicative of the patient's autoregulation status (e.g., a degree of impairment) to the output device 18, as discussed above with respect to FIG. 1.

It should be understood that Equation (1) is not intended to be limiting, and is merely provided as an example of a dynamic model that may be used to monitor the patient's autoregulation status. Various models may be utilized in accordance with the systems and methods disclosed herein. For example, finite element, finite different, or wave tracing models may be used to monitor the patient's autoregulation. Furthermore, the systems and methods disclosed herein may utilize complex dynamic models that account for multi-path vasculature or the like. Additionally, in some embodiments, the model may include a delay differential equation or time shift the forcing function (e.g., P*) prior to fitting the model to patient data to account for the inherent delay between changes in blood pressure and the oxygen saturation response and to facilitate parameterization of the patient's autoregulation system.

In some embodiments, the controller 16 may be configured to monitor the patient's autoregulation status by constantly and/or routinely (e.g., every 5, 10, 30, 60, 120 seconds or more) fitting the model to patient data as set forth herein. In other embodiments, the controller 16 may be configured to fit the model to patient data only after a step change (e.g., a distinct change) in blood pressure is detected by the controller 16. For example, the controller 16 may enter into an autoregulation monitoring mode in which the model is fitted to patient data after a change (e.g., greater than 1, 5, 10, 25 percent) in blood pressure is detected. In such cases, the controller 16 may monitor the patient's autoregulation status for a period of time (e.g., 1, 5, 10 minutes or more) after the step change is detected by constantly and/or routinely (e.g., every 5, 10, 30, 60, 120 seconds or more) fitting the model to patient data as set forth herein during the autoregulation monitoring mode.

Figure 4:
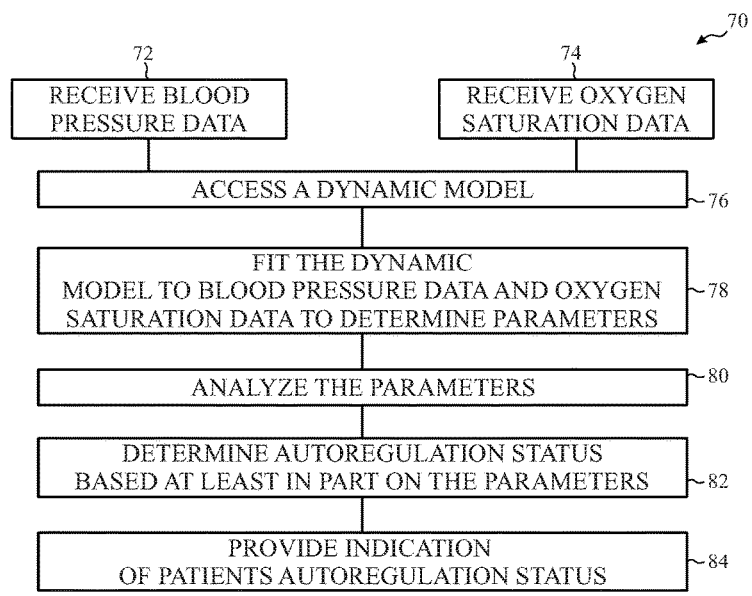
FIG. 4 is a process flow diagram of a method of monitoring autoregulation, in accordance with an embodiment.

FIG. 4 is a process flow diagram of a method 70 of monitoring autoregulation, in accordance with an embodiment. The method 70 includes various steps represented by blocks. The method 70 may be performed as an automated procedure by a system, such as system 10. Although the flow chart illustrates the steps in a certain sequence, it should be understood that the steps may be carried out in any suitable order, certain steps may be carried out simultaneously, and/or certain steps may be omitted, where appropriate. Further, certain steps or portions of the method 70 may be performed by separate devices. For example, a first portion of the method 70 may be performed by the controller 16, while a second portion of the method 70 may be performed by the sensor 14. In addition, insofar as steps of the method disclosed herein is applied to the received signals, it should be understood that the received signals may be raw signals or processed signals. That is, the method 70 may be applied to an output of the received signals.

In step 72, the controller 16 may receive the blood pressure signal (e.g., arterial blood pressure signal). In some embodiments, the controller 16 may receive the blood pressure signal from the blood pressure sensor 12, as set forth above. In step 74, the controller 16 may receive the oxygen saturation signal. In some embodiments, the controller 16 may receive the oxygen saturation signal from the oxygen saturation sensor 14, as set forth above.

In step 76, the controller 16 may access a dynamic model from a memory, such as the memory device 26. In certain embodiments, the controller 16 may select an appropriate dynamic model from a plurality of dynamic models stored in the memory device 26. For example, the controller 16 may select the dynamic model constructed for the particular patient (e.g., based on data previously obtained from the patient and/or based on characteristics (e.g., age, gender, physiological condition, or the like) of the monitored patient as input by a user and/or a sensor.

In step 78, the controller 16 may fit the dynamic model to the blood pressure data of the blood pressure signal and the oxygen saturation data of the oxygen saturation signal. In particular, the controller 16 may be configured to determine (e.g., estimate and/or optimize) one or more parameters (e.g., A, a, B, b, C, and c in Equation (1)) defining the dynamic behavior of the model. For example, the controller 16 may be configured to adjust one or more parameters through a parametric search using the blood pressure signal input (e.g., P* in Equation (1)) until the dynamic model matches the oxygen saturation signal output (e.g., x in Equation (1)).

In step 80, the controller 16 may analyze the parameters (e.g., compare the one or more determined parameters to predetermined respective ranges, values, and/or thresholds stored in the memory device 26, or any other suitable memory device). In step 82, the controller 16 may determine the patient's autoregulation status based at least in part on the one or more determined parameters and/or the comparison of the one or more determined parameters as set forth in step 80. Certain parameter values or combinations of parameter values may indicate intact autoregulation, while some values may indicate moderately impaired autoregulation, and other values may indicate severely impaired autoregulation, for example.

In step 84, the controller 16 may output an indication of the patient's autoregulation status to the output device 18. For example, the controller 16 may be configured to generate an alarm signal indicative of the patient's autoregulation status and to provide the alarm signal to the output device 18. Additionally or alternatively, the controller 16 may be configured to generate a signal that causes the output device 18 to visually (e.g., via a display) and/or audibly (e.g., via a speaker) output information indicative of the patient's autoregulation status (e.g., the estimated parameters, a graph, a numerical indicator, a text message, or the like). The method 70 may enable parameterization of the patient's autoregulation status, and thus, may enable accurate and/or precise determination of autoregulation status.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that certain elements of the disclosed embodiments may be combined or exchanged with one another.

What is claimed is:

1. A method for monitoring autoregulation, the method comprising:
   receiving, by one or more processors, blood pressure data and oxygen saturation data from a patient;
   detecting, by the one or more processors, a step change in a blood pressure of the patient based on the blood pressure data;
   fitting, by the one or more processors, a dynamic model to the blood pressure data and the oxygen saturation data to determine one or more parameters of the dynamic model indicative of autoregulation only after the step change in the blood pressure is detected, wherein the dynamic model indicates a response of oxygen saturation to a change in blood pressure; and
   determining, by the one or more processors, the patient's autoregulation status based on the one or more parameters.

2. The method of claim 1, wherein determining the patient's autoregulation status comprises comparing the one or more parameters to predetermined values, ranges, or thresholds.

3. The method of claim 1, wherein determining the patient's autoregulation status comprises determining a degree of impairment of the patient's autoregulation system based on the one or more parameters.

4. The method of claim 1, wherein the dynamic model comprises a differential equation model.

5. The method of claim 1, wherein the dynamic model comprises a damped dynamic oscillator model.

6. The method of claim 1, wherein the dynamic model has the following form:

$$Ax^a + Bx^b + Cx^c + D = P^*,$$

where x is an oxygen saturation value, $P^*$ is a pressure forcing function, D is a constant, and A, a, B, b, C, and c are parameters.

7. The method of claim 1, wherein the dynamic model comprises a finite element model, a finite difference model, a wave tracing model, or a delay differential equation.

8. The method of claim 1, further comprising constructing the dynamic model based on empirical data.

9. The method of claim 1, further comprising providing, by the one or more processors, an indication of the patient's autoregulation status on a display.

10. A non-transitory computer-readable medium having computer executable code stored thereon, the code comprising instructions that, when executed by one or more processors, cause the one or more processors to:
    receive blood pressure data and oxygen saturation data from a patient;
    detect a step change in a blood pressure of the patient based on the blood pressure data;
    fit a dynamic model to the blood pressure data and the oxygen saturation data to determine one or more parameters of the dynamic model indicative of autoregulation only after the step change in the blood pressure is detected, wherein the dynamic model indicates a response of oxygen saturation to a change in blood pressure; and
    determine the patient's autoregulation status based on the one or more parameters.

11. The non-transitory computer-readable medium of claim 10, wherein the code comprises instructions that, when executed by the one or more processors, cause the one or more processors to determine the patient's autoregulation status by at least comparing the one or more parameters to predetermined values, ranges, or thresholds.

12. The non-transitory computer-readable medium of claim 10, wherein the dynamic model comprises a damped dynamic oscillator model.

13. A system for monitoring autoregulation, the system comprising:
    an oxygen saturation sensor configured to obtain oxygen saturation data from a patient; and
    a controller comprising one or more processors configured to:
      receive blood pressure data indicative of blood pressure of the patient and receive the oxygen saturation data;
      detect a step change in a blood pressure of the patient based on the blood pressure data;
      fit a dynamic model to the blood pressure data and the oxygen saturation data to determine one or more parameters of the dynamic model indicative of autoregulation only after the step change in the blood pressure is detected, wherein the dynamic model indicates a response of oxygen saturation to a change in blood pressure; and
      determine the patient's autoregulation status based on the one or more parameters.

14. The system of claim 13, wherein the one or more processors are configured to determine the patient's autoregulation status by at least comparing the one or more parameters to predetermined values, ranges, or thresholds.

15. The system of claim 13, wherein the one or more processors are configured to determine the patient's autoregulation status by at least determining a degree of impairment of the patient's autoregulation system based on the one or more parameters.

16. The system of claim 13, wherein the dynamic model comprises a damped dynamic oscillator model.

17. The system of claim 13, further comprising a display, and wherein the one or more processors are configured to output an indication of the patient's autoregulation status to the display.

18. The system of claim 13, wherein the dynamic model has the following form:

$$A\ddot{x}^a + B\dot{x}^b + Cx^c + D = P^*,$$

where x is an oxygen saturation value, P* is a pressure forcing function, D is a constant, and A, a, B, b, C, and c are parameters.

19. The system of claim 13, wherein the dynamic model comprises a finite element model, a finite difference model, a wave tracing model, or a delay differential equation.

* * * * *